(12) United States Patent
Horisaka et al.

(10) Patent No.: US 9,091,646 B2
(45) Date of Patent: Jul. 28, 2015

(54) GAS SENSOR AND METHOD FOR MANUFACTURING SAME

(75) Inventors: Sumiko Horisaka, Nagoya (JP); Hiroki Fujita, Kasugai (JP); Mika Murakami, Nagoya (JP); Takashi Ito, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 407 days.

(21) Appl. No.: 13/013,094

(22) Filed: Jan. 25, 2011

(65) Prior Publication Data

US 2011/0186431 A1 Aug. 4, 2011

(30) Foreign Application Priority Data

Feb. 2, 2010 (JP) ................................. 2010-021430

(51) Int. Cl.
*G01N 27/26* (2006.01)
*G01N 27/407* (2006.01)
*G01N 33/00* (2006.01)

(52) U.S. Cl.
CPC ........ *G01N 27/4077* (2013.01); *G01N 27/4075* (2013.01); *G01N 33/0037* (2013.01)

(58) Field of Classification Search
CPC  G01N 27/4077; G01N 27/04; G01N 33/0037
USPC ................................................ 204/421–428
See application file for complete search history.

(56) References Cited

U.S. PATENT DOCUMENTS

| | | |
|---|---|---|
| 2003/0034245 A1* | 2/2003 | Diehl ............................ 204/424 |
| 2003/0159928 A1* | 8/2003 | Kojima et al. ................. 204/408 |
| 2006/0283708 A1* | 12/2006 | Ando et al. .................... 204/424 |
| 2007/0007136 A1* | 1/2007 | Awano et al. .................. 204/424 |

FOREIGN PATENT DOCUMENTS

| | | |
|---|---|---|
| DE | 101 22 271 A1 | 12/2002 |
| EP | 857966 A2 * | 8/1998 |
| EP | 1 445 607 A1 | 8/2004 |
| JP | 2005-156471 A1 | 6/2005 |
| JP | 2005-195516 A1 | 7/2005 |
| JP | 2006-343297 A1 | 12/2006 |

(Continued)

OTHER PUBLICATIONS

J. Reigel, et al., "Exhaust Gas Sensors for Automotive Emission Control," Solid State Ionics, vol. 152-153, Dec. 1, 2002, pp. 783-800.

*Primary Examiner* — Keith Hendricks
*Assistant Examiner* — Kourtney S Carlson
(74) *Attorney, Agent, or Firm* — Burr & Brown, PLLC (57) ABSTRACT

A NOx sensor 100 includes a sensor device 110 and a heater 70 capable of heating the sensor device 110. The sensor device 110 includes an inner pump electrode 22 and an outer pump electrode 23 disposed respectively on the inner side and the outer side of a solid electrolyte layer 6. The sensor device 110 detects the concentration of NOx by introducing a gas to be measured into a first inner vacancy 20, pumping out oxygen in the gas to be measured from the inner pump electrode 22 to the outer pump electrode 23, introducing the gas to be measured, from which the oxygen has been pumped out, into a second inner vacancy 40, reducing the NOx in the gas to be measured, to thereby generate oxygen, and detecting the generated oxygen. A characteristic stabilizing layer 24 covers the outer pump electrode 23 and is made of a porous body with a thickness of 10 to 200 μm and a thickness variation of 20% or less.

11 Claims, 5 Drawing Sheets

(56) References Cited

FOREIGN PATENT DOCUMENTS

| JP | 2007-033464 A1 | 2/2007 |
|---|---|---|
| JP | 2007-040838 A1 | 2/2007 |
| JP | 2008-164411 A1 | 7/2008 |
| JP | 2009-236833 A1 | 10/2009 |

* cited by examiner

※Circled numbers correspond Example numbers

FIG. 8

GAS SENSOR AND METHOD FOR MANUFACTURING SAME

FIELD OF THE INVENTION

The present invention relates to a gas sensor and a method for manufacturing the gas sensor.

BACKGROUND OF THE INVENTION

Hitherto, a NOx sensor has been known as a thick-film multilayer gas sensor of the limiting current type. The NOx sensor includes a sensor device (element) for detecting the concentration of NOx in a gas to be measured (i.e., a gas under measurement), and a heater disposed adjacent to the sensor device. The sensor device includes an inner pump electrode and an outer pump electrode disposed on the inner side and the outer side of a base member, respectively, which is made of a solid electrolyte layer having oxygen-ion conductivity. The inner pump electrode introduces the gas under the measurement into a first chamber that is exposed to the outside, and then pumps out oxygen in the gas under the measurement from the inner pump electrode to the outer pump electrode. The gas under the measurement, from which the oxygen has been pumped out, is introduced to a second chamber where NOx in the gas under the measurement is reduced to generate oxygen. The generated oxygen is detected to detect the concentration of NOx. The heater serves to perform temperature adjustment by heating the sensor device and holding it at a predetermined temperature.

In one proposed example of the above-described NOx sensor, a porous protective layer made of alumina, for example, is disposed so as to cover the outer pump electrode (see Patent Document 1). According to the proposed NOx sensor, the porous protective layer serves to prevent an oil component, etc., which are contained in the gas under the measurement, from being attached to the outer pump electrode.

In another proposed example of the above-described NOx sensor, a porous alumina sintered compact having communicating pores with a mean pore size of 500 to 1100 Å and a porosity of 6 to 16% is formed as an electrode protective layer on the surface of at least one of a pair of electrodes of a pump cell (see Patent Document 2). According to the proposed NOx sensor, even after use for a long period, it is possible to prevent a reduction of an output in detection of the gas under the measurement, and to ensure a stable detection output of the gas under the measurement. Similar techniques are further described in Patent Documents 3 and 4.

Patent Document 1: JP2008-164411A
Patent Document 2: JP 2005-156471A
Patent Document 3: JP2005-195516A
Patent Document 4: JP2006-343297A

SUMMARY OF THE INVENTION

In the NOx sensor, when the temperature of the sensor device lowers, the heater heats the sensor device such that the temperature of the sensor device is adjusted to the predetermined temperature. However, if the ambient temperature of the sensor device lowers abruptly such as occurred when a flow rate of the gas under the measurement is abruptly increased, there arises a problem that the impedance between the inner pump electrode and the outer pump electrode is increased due to a delay in the temperature adjustment by the heater and hence measurement accuracy is reduced. Improvements to overcome such a problem have been addressed by covering the outer pump electrode with the porous protective layer as described in Patent Documents 1 to 4.

However, it has been confirmed that the technique of simply covering the outer pump electrode with the porous protective layer, as described in Patent Document 1, is not sufficient as a countermeasure to cope with abrupt cooling at the surface of the sensor device. Also, another problem has been confirmed in that a time from start of operation of the sensor until reaching a stabilized state of a sensor signal (i.e., a light-off time) is not constant among products. In Patent Documents 3 and 4, the porous protective layer is formed by printing a paste over an entire periphery of a fore end of a laminate that has been fired (fired) in advance, and by firing the paste again. However, such a method causes a still another problem that because a warp occurs in the laminate during the first firing and a pattern printed thereafter cannot exactly follow the surface of the laminate, a variation in thickness of the porous protective layer tends to increase excessively.

The present invention has been accomplished with the view of solving the above-described problems, and a main object of the present invention is to provide a gas sensor which can maintain a high level of measurement accuracy and can prevent the light-off time from becoming longer or from varying among products, even when the ambient temperature lowers abruptly.

The present invention provides a gas sensor comprising a sensor device including an inner pump electrode and an outer pump electrode disposed respectively on an inner side and an outer side of a base member made of a solid electrolyte layer having oxygen-ion conductivity, the sensor device detecting concentration of a particular gas in an object gas to be measured with operations of introducing the object gas into a gas chamber to which the inner pump electrode is exposed and pumping out oxygen in the gas chamber to the outside from the inner pump electrode through the outer pump electrode, and a heater disposed adjacent to the sensor device to be capable of heating the sensor device, wherein the gas sensor further comprises a characteristic stabilizing layer covering the outer pump electrode and made of a porous body with a thickness of 10 to 200 µm and a thickness variation of 20% or less.

Herein, examples of the "particular gas" include NOx, $O_2$, $NH_3$, $CO_2$, and $H_2O$. When detecting the concentration of NOx, the concentration of NOx is detected by disposing the inner pump electrode and the outer pump electrode respectively on the inner side and the outer side of the base member, which is made of the solid electrolyte layer having oxygen-ion conductivity, introducing the object gas into a first chamber to which the inner pump electrode is exposed, pumping out oxygen in the object gas from the inner pump electrode to the outer pump electrode, introducing the object gas, from which the oxygen has been pumped out, into a second chamber, reducing a NOx gas in the object gas, to thereby generate oxygen, and detecting the generated oxygen. The concentration of $O_2$, $CO_2$, or $H_2O$ can also be detected on the basis of the same principle. In the case of $NH_3$, $NH_3$ is first oxidized to generate NOx, and the concentration of NOx is detected on the basis of the same principle. Thereafter, the detected concentration of NOx is converted to the concentration of $NH_3$.

In the gas sensor thus constructed, the outer pump electrode is covered with the characteristic stabilizing layer having an appropriate thickness and an appropriate thickness variation. Therefore, even when the ambient temperature of the sensor device lowers abruptly, measurement accuracy can be maintained at a high level, and the light-off time can be prevented from becoming longer or from varying among products.

More specifically, if the thickness of the characteristic stabilizing layer is less than 10 μm, the thermal capacity is so small that, when the ambient temperature lowers abruptly, the temperature of the outer pump electrode also lowers and the measurement accuracy decreases correspondingly. In contrast, when the thickness of the characteristic stabilizing layer is 10 μm or more, the thermal capacity is sufficiently large, whereby the temperature of the outer pump electrode is not so reduced and the measurement accuracy is maintained at a high level even when the ambient temperature lowers abruptly. Also, if the thickness of the characteristic stabilizing layer exceeds 200 μm, the oxygen pumped out to the outer pump electrode cannot be easily purged and the light-off time is prolonged. In contrast, when the thickness of the characteristic stabilizing layer is 200 μm or less, the oxygen pumped out to the outer pump electrode can be easily purged at a sufficient level in comparison with the amount of pumped-out oxygen, and the light-off time can be avoided from becoming longer. Further, if the thickness variation of the characteristic stabilizing layer exceeds 20%, the purging of the oxygen having been pumped out to the outer pump electrode is so uneven that a variation in the light-off time among the products is increased abruptly. In contrast, when the thickness variation of the characteristic stabilizing layer is 20% or less, the variation in the light-off time among the products can be held small.

In the gas sensor according to the present invention, the characteristic stabilizing layer preferably has a thickness of 10 to 100 μm. With such a feature, the oxygen having been pumped out to the outer pump electrode is more evenly purged and the light-off time can be shortened.

The gas sensor according to the present invention may further comprise a firing strain prevention layer formed on a surface of the sensor device opposite to a surface thereof on which the characteristic stabilizing layer is provided. A ceramic is produced by compacting a mixture of powder and a binder or powder alone, and by firing an obtained compact. With evaporation of the binder and sintering of powder particles, however, firing shrinkage always occurs during the firing and the size of the ceramic after the firing is smaller than that before the firing. When a ceramic product is fabricated by compacting various ceramics differing in material and shape in a combined state, shrinkages occur in an unbalanced state during the firing because behaviors in firing shrinkages of those ceramics differ from one another. Hence, firing distortions (warp and torsion) are apt to occur. In the ceramic product fabricated by compacting various ceramics differing in material and shape in a combined state, it is usual to prevent the firing distortions (warp and torsion) by modifying designs on a trial-and-error basis while changing the materials and the shapes. In the gas sensor according to the present invention, the firing strain prevention layer may be formed on a surface of the sensor device opposite to a surface thereof on which the characteristic stabilizing layer is provided. Preferably, the firing strain prevention layer is made of the same material and has the same shape and thickness as those of the characteristic stabilizing layer. With those features, the firing shrinkages occur similarly in both the surface on which the characteristic stabilizing layer is disposed and the surface on the opposite side to the former surface. Accordingly, even when the gas sensor is subjected to the firing step in manufacturing the gas sensor, the occurrence of a warp during the firing step can be prevented. In this respect, the firing strain prevention layer is preferably disposed at a position opposed to the characteristic stabilizing layer. In addition, the firing strain prevention layer may be further formed on both lateral surfaces of the gas sensor. With that feature, since the firing shrinkages occur similarly among four surface of the gas sensor, the occurrence of torsion can also be prevented.

The gas sensor according to the present invention may further comprise a thermal insulation layer formed on a surface of the sensor device in which a gas inlet port for introducing the object gas into the gas chamber is provided. With such a feature, since the thermal insulation effect is enhanced, power consumption of the heater can be further reduced. The thermal insulation layer is disposed so as not to close the gas inlet port. When the thermal insulation layer is porous to be able to introduce gas therethrough, the thermal insulation layer may be disposed in a state closing the gas inlet port in an outer topographic appearance.

The present invention also provides a method for manufacturing the above-described gas sensor, the method comprising the steps of:

(a) preparing a plurality of unfired green sheets used to form the sensor device and the heater;

(b) stacking the unfired green sheets to form a laminate, and screen-printing slurry as a material forming the characteristic stabilizing layer, to cover a portion of the laminate with the slurry, the portion serving as the outer pump electrode (hereinafter referred to as a "stacking-printing step"); and (c) firing the laminate obtained in the step (b).

The present invention also provides a method for manufacturing the above-described gas sensor, the method comprising the steps of:

(a) preparing a plurality of unfired green sheets used to form the sensor device and the heater;

(b) screen-printing slurry as a material forming the characteristic stabilizing layer on one of the unfired green sheets, which includes a portion serving as the outer pump electrode, to cover the portion with the slurry, and thereafter stacking the unfired green sheets to form a laminate (hereinafter referred to as a "printing-stacking step"); and (c) firing the laminate obtained in the step (b).

With the gas sensor manufacturing method described above, the laminate is fired after screen-printing the slurry, which is a material to form the characteristic stabilizing layer in the stage before the firing. Therefore, even when the base member made of the solid electrolyte layer is warped during the firing, the outer pump electrode and the characteristic stabilizing layer are also warped correspondingly. As a result, the characteristic stabilizing layer is deformed to follow the shapes of the base member and the outer pump electrode, and the thickness variation thereof is less apt to occur. Accordingly, it is possible to easily hold not only the thickness of the characteristic stabilizing layer in the gas sensor to be in the range of 10 to 200 μm, but also the thickness variation thereof to be 20% or less.

When the above-described gas sensor including the characteristic stabilizing layer is manufactured, according to the present invention, it is preferable that the step (b) further performs screen-printing slurry as a material forming the firing strain prevention layer to cover a portion of the laminate with the slurry, the portion serving as the firing strain prevention layer, after stacking the unfired green sheets to form a laminate. Also, it is preferable that the step (b) further perform screen-printing slurry as a material forming the firing strain prevention layer on at least one surface of one or more of the unfired green sheets, on which the firing strain prevention layer is to be formed, prior to stacking the unfired green sheets to form a laminate.

When the above-described gas sensor including the thermal insulation layer is manufactured, according to the present invention, the step (c) may form the thermal insulation layer by screen-printing the slurry on a surface of the laminate, in which the gas inlet port for introducing the object gas into the gas chamber is formed, in a state not closing the gas inlet port, before or after cutting the laminate obtained in the step (b) into a shape corresponding to each of individual gas sensors, and thereafter fire the laminate.

DETAILED DESCRIPTION OF THE INVENTION

Figure 1:
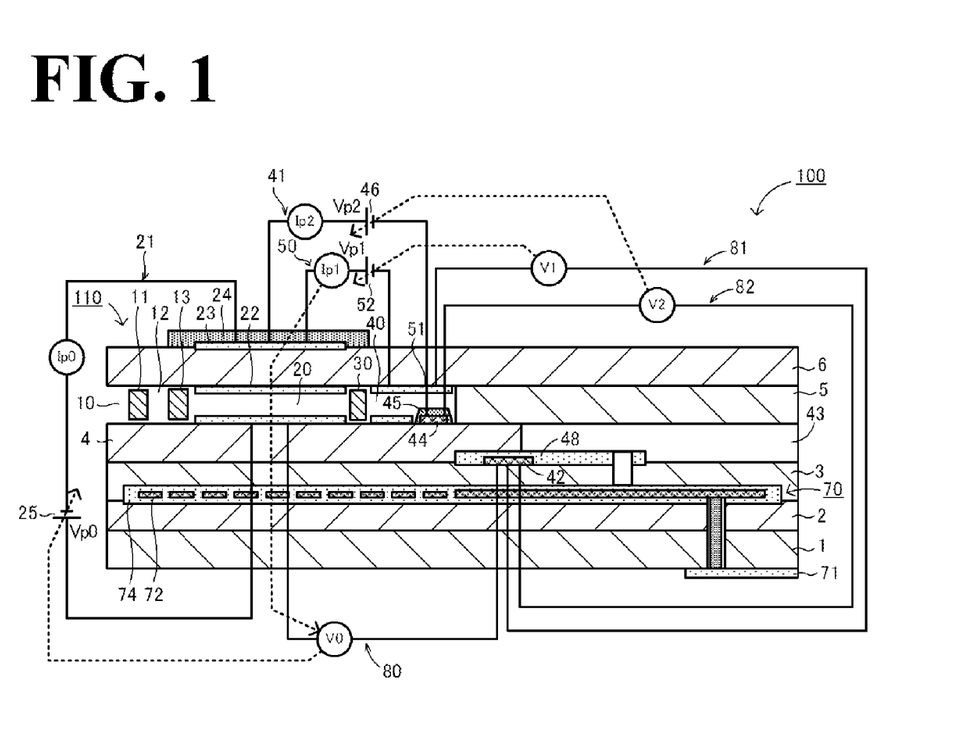
FIG. 1 is a vertical sectional view illustrating principal components of a NOx sensor 100.

Embodiments of the present invention will be described below with reference to the drawings. FIG. 1 is a vertical sectional view illustrating principal components of a NOx sensor 100.

The NOx sensor 100 includes a sensor device 110 for detecting the concentration of NOx in a gas to be measured (i.e., a gas under measurement), and a heater 70 disposed adjacent to the sensor device 110. The NOx sensor 100 has a structure in which six layers, including a first substrate layer 1, a second substrate layer 2, and a third substrate layer 3, each being made of a solid electrolyte layer having oxygen-ion conductivity, such as zirconia ($ZrO_2$), as well as a first solid electrolyte layer 4, a spacer layer 5, and a second solid electrolyte layer 6, are stacked from the lower side, as viewed in FIG. 1, in the order in which they are named. A solid electrolyte used to form those six layers is compact in texture. The structure and the operation principle of the above-described NOx sensor 100 are known (see, e.g., JP2008-164411A).

The sensor device 110 is formed by stacking the first solid electrolyte layer 4, the spacer laser 5, and the second solid electrolyte layer 6. Between a lower surface of the second solid electrolyte layer 6 and an upper surface of the first solid electrolyte layer 4 in the sensor device 110, a gas inlet port 10, a first diffusion rate-limiting portion 11, a buffer space 12, a second diffusion rate-limiting portion 13, a first inner vacancy 20, a third diffusion rate-limiting portion 30, and a second inner vacancy 40 are formed in the named order from a fore end (left end in FIG. 1) of the sensor device 110 toward the inner side to be communicated with each other in a successive manner. The gas inlet port 10, the buffer space 12, the first inner vacancy 20, and the second inner vacancy 40 are formed in a space prepared by partly cutting out the spacer layer 5 to provide a hollow portion. The hollow space is defined such that its upper side is demarcated by the lower surface of the second solid electrolyte layer 6, its lower side is demarcated by the upper surface of the first solid electrolyte layer 4, and its lateral sides are demarcated by wall surfaces of the hollow space itself cut out in the spacer layer 5. The first diffusion rate-limiting portion 11, the second diffusion rate-limiting portion 13, and the third diffusion rate-limiting portion 30 are each provided in the form of two horizontally elongate slits (each having an opening of which length direction is aligned with the direction perpendicular to the drawing sheet). A portion extending from the gas inlet port 10 to the second inner vacancy 40 is also called a gas communicating portion.

Further, a reference gas inlet space 43 is formed at a position farther away from the fore end of the sensor device 110 than the gas communicating portion. The reference gas inlet space 43 is a space prepared by partly cutting out the first solid electrolyte layer 4 to provide a hollow portion, and is defined such that its upper side is demarcated by a lower surface of the spacer layer 5, its lower side is demarcated by an upper surface of the third substrate layer 3, and its lateral sides are demarcated by wall surfaces of the hollow space cut out in the first solid electrolyte layer 4. Atmospheric air, for example, is introduced to the reference gas inlet space 43 as a reference gas in measuring the concentration of NOx. An atmosphere inlet layer 48 is a layer made of porous alumina and disposed between the first solid electrolyte layer 4 and the third substrate layer 3. The reference gas is introduced to the atmosphere inlet layer 48 through the reference gas inlet space 43. The atmosphere inlet layer 48 is formed so as to cover a reference electrode 42. The reference electrode 42 is an electrode formed between the upper surface of the third substrate layer 3 and a lower surface of the first solid electrolyte layer 4. As described above, the atmosphere inlet layer 48 communicating with the reference gas inlet space 43 is disposed around the reference electrode 42. In addition, as described later, the oxygen concentration (oxygen partial pressure) within each of the first inner vacancy 20 and the second inner vacancy 40 can be measured by using the reference electrode 42.

The first inner vacancy 20 is provided as a space for adjusting the oxygen partial pressure in the gas under the measurement, which is introduced through the second diffusion rate-limiting portion 13. The oxygen partial pressure is adjusted with operation of a main pump cell 21. The main pump cell 21 is an electrochemical pump cell constituted by an inner pump electrode 22 formed in a tunnel-like shape within the first inner vacancy 20, an outer pump electrode 23 disposed on the surface of the second solid electrolyte layer 6 on the opposite side to the inner pump electrode 22, and the second solid electrolyte layer 6 sandwiched between both the electrodes 22 and 23. The inner pump electrode 22 and the outer pump electrode 23 are each formed as a porous cermet electrode (e.g., a cermet electrode made of Pt with Au of 1% and $ZrO_3$).

The outer pump electrode 23 is covered with a characteristic stabilizing layer 24. The characteristic stabilizing layer 24 is made of a porous body having a thickness of 10 to 200 µm, preferably 10 to 100 µm, and a thickness variation of 20% or less. The characteristic stabilizing layer 24 is not limited to a particular material as long as it is a porous body. Examples of the porous body include an alumina porous body, a zirconia porous body (zirconia may be either partially stabilized zirconia or perfectly stabilized zirconia), a spinel porous body, and a cordierite porous body. The porous body may be added with sodium, potassium, calcium, magnesium, barium, aluminum, zirconium, and/or silicon as required. Further, the characteristic stabilizing layer 24 has a porosity of preferably 10 to 65%, more preferably 10 to 50%. If the porosity is less than 10%, an unsatisfactory result would arise in that oxygen having been pumped out to the outer pump electrode cannot be easily purged. If the porosity exceeds 65%, an unsatisfactory result would arise in that the characteristic stabilizing layer cannot be obtained with sufficient strength.

In the main pump cell 21, oxygen in the first inner vacancy 20 can be pumped out to an outer space, or oxygen in the outer space can be pumped into the first inner vacancy 20 by applying a desired pump voltage Vp0 between the inner pump electrode 22 and the outer pump electrode 23 so that a pump current Ip0 flows between the inner pump electrode 22 and the outer pump electrode 23 in a positive direction or a negative direction.

To detect the oxygen concentration (oxygen partial pressure) in an atmosphere within the first inner vacancy 20, an electrochemical sensor cell, i.e., an oxygen partial-pressure detecting sensor cell 80 for main pump control, is constituted by the inner pump electrode 22, the second solid electrolyte layer 6, the spacer layer 5, the first solid electrolyte layer 4, the third substrate layer 3, and the reference electrode 42. The oxygen concentration (oxygen partial pressure) in the first inner vacancy 20 can be determined by measuring an electromotive force V0 that is generated in the oxygen partial-pressure detecting sensor cell 80. Further, the pump current Ip0 is controlled by performing feedback control of a variable power supply 25 (voltage Vp0) such that the electromotive force V0 is held constant. As a result, the oxygen concentration in the first inner vacancy 20 can be held at a predetermined constant value.

The second inner vacancy 40 is a space to perform treatment regarding the measurement of the concentration of NOx in the gas under the measurement, which is introduced through the third diffusion rate-limiting portion 30. The third diffusion rate-limiting portion 30 serves to guide the gas under the measurement to the second inner vacancy 40 while applying predetermined diffusion resistance to the gas under the measurement in which the oxygen concentration (oxygen partial pressure) has been controlled in the first inner vacancy 20 with the operation of the main pump cell 21.

In the second inner vacancy 40, the adjustment of the oxygen concentration (oxygen partial pressure) is further performed by an auxiliary pump cell 50 on the gas under the measurement, which is introduced through the third diffusion rate-limiting portion 30 after the oxygen concentration (oxygen partial pressure) has been previously adjusted in the first inner vacancy 20. As a result, the oxygen concentration in the second inner vacancy 40 can be held constant with high accuracy, and hence the concentration of NOx can be measured with high accuracy.

The auxiliary pump cell 50 is an auxiliary electrochemical pump cell constituted by an auxiliary pump electrode 51 formed in a tunnel-like shape within the second inner vacancy 40, the outer pump electrode 23, and the second solid electrolyte layer 6.

In the auxiliary pump cell 50, oxygen in an atmosphere within the second inner vacancy 40 can be pumped out to the outer space, or oxygen in the outer space can be pumped into the second inner vacancy 40 by applying a desired voltage Vp1 between the auxiliary pump electrode 51 and the outer pump electrode 23.

To control the oxygen partial pressure in the atmosphere within the second inner vacancy 40, an electrochemical sensor cell, i.e., an oxygen partial-pressure detecting sensor cell 81 for auxiliary pump control, is constituted by the auxiliary pump electrode 51, the reference electrode 42, the second solid electrolyte layer 6, the spacer layer 5, the first solid electrolyte layer 4, and the third substrate layer 3. The oxygen partial-pressure detecting sensor cell 81 detects an electromotive force V1 that is generated between the auxiliary pump electrode 51 and the reference electrode 42. The auxiliary pump cell 50 performs pumping with a variable power supply 52 (voltage Vp1), which voltage is controlled in accordance with the electromotive force V1. As a result, the oxygen partial pressure in the atmosphere within the second inner vacancy 40 can be controlled to such a low level of partial pressure that the measurement of NOx is substantially unaffected. In addition, the pump current Ip1 of the auxiliary pump cell 50 is used to control the electromotive force V0 of the oxygen partial-pressure detecting sensor cell 80 for main pump control. As a result, a gradient of the oxygen partial pressure in the gas under the measurement, which is introduced to the second inner vacancy 40 from the third diffusion rate-limiting portion 30, can be always held constant.

A measurement pump cell 41 measures the concentration of NOx in the gas under the measurement inside the second inner vacancy 40. The measurement pump cell 41 is an electrochemical pump cell that is constituted by a measurement electrode 44, the outer pump electrode 23, the second solid electrolyte layer 6, the spacer layer 5, and the first solid electrolyte layer 4. The measurement electrode 44 is disposed on the upper surface of the first solid electrolyte layer 4, which faces the second inner vacancy 40, at a position away from the third diffusion rate-limiting portion 30. The measurement electrode 44 is a porous cermet electrode having substantially a rectangular shape in a plan view. The measurement electrode 44 functions also as a NOx reduction catalyst for reducing NOx that is present in the atmosphere within the second inner vacancy 40. Further, the measurement electrode 44 is covered with a fourth diffusion rate-limiting portion 45. The fourth diffusion rate-limiting portion 45 is in the form of a film made of a porous body containing alumina ($Al_2O_3$) as a main component. The fourth diffusion rate-limiting portion 45 not only has a role of limiting the amount of NOx flowing toward the measurement electrode 44, but also serves as a protective film for the measurement electrode 44.

The measurement pump cell 41 pumps out oxygen generated with decomposition of NOx in an atmosphere around the measurement electrode 44 so that the amount of generated oxygen can be detected as a pump current Ip2 flowing between the measurement electrode 44 and the outer pump electrode 23.

To detect the oxygen partial pressure around the measurement electrode 44, an electrochemical sensor cell, i.e., an oxygen partial-pressure detecting sensor cell 82 for measurement-pump control, is constituted by the second solid electrolyte layer 6, the spacer layer 5, the first solid electrolyte layer 4, the third substrate layer 3, the measurement electrode 44, and the reference electrode 42. A variable power supply 46 (voltage Vp2) for the measurement pump cell 41 is controlled in accordance with an electromotive force V2 that is detected by the oxygen partial-pressure detecting sensor cell 82 for measurement-pump control.

The gas under the measurement, which has been guided to the second inner vacancy 40, reaches the measurement electrode 44 through the fourth diffusion rate-limiting portion 45 is a situation where the oxygen partial pressure is controlled. NOx in the gas under the measurement around the measurement electrode 44 is reduced to generate oxygen ($2NO \rightarrow N_2 + O_2$). The generated oxygen is then pumped by the measurement pump cell 41. At that time, the voltage Vp2 of the variable power supply 46 is controlled so that the electromotive force V2 detected by the oxygen partial-pressure detecting sensor cell 82 for measurement-pump control is held constant. Because the amount of oxygen generated around the measurement electrode 44 is proportional to the concentration of NOx in the gas under the measurement, the concentration of NOx in the gas under the measurement can be calculated based on the pump current Ip2 flowing in the measurement pump cell 41. A practical procedure for deriving the concentration of NOx is as follows. The pump current Ip2 resulting when a sample gas containing no NOx is introduced is measured as an offset current in advance. A pump current difference ΔIp2 is obtained by subtracting the offset current from the pump current Ip2 resulting when an actual gas to be measured is introduced. The concentration of NOx is calculated from the amount of oxygen corresponding to the pump current difference ΔIp2.

In the NOx sensor 100 constructed as described above, the gas under the measurement is supplied to the measurement pump cell 41 in such a state that the oxygen partial pressure in the gas under the measurement is always held at a constant low value (i.e., a value substantially not affecting the measurement of NOx) with operations of the main pump cell 21 and the auxiliary pump cell 50. Accordingly, oxygen generated through reduction of NOx almost in proportion to the concentration of NOx in the gas under the measurement is pumped out by the measurement pump cell 41. Hence, the concentration of NOx in the gas under the measurement can be determined based on the pump current Ip2 flowing with the pumping of the generated oxygen.

The heater 70 is formed in a position sandwiched between the second substrate layer 2 and the third substrate layer 3. The heater 70 serves to perform temperature adjustment by heating the sensor device 110 and holding it at a predetermined temperature in order to increase the oxygen-ion conductivity of the solid electrolyte in each layer. The heater 70 includes a heater electrode 71, a resistance heating element 72, and a heater insulation layer 74. The heater electrode 71 is formed in contact with a lower surface of the first substrate layer 1. The heater electrode 71 is connected to an external power supply (not shown) for supplying electric power to the resistance heating element 72 from the outside. The resistance heating element 72 is connected to the heater electrode 71. The resistance heating element 72 is buried over an entire region ranging from the first inner vacancy 20 to the second inner vacancy 40 such that the entirety of the NOx sensor 100 can be adjusted to temperature at which the solid electrolyte is activated. The heater insulation layer 74 is made of an insulator, e.g., alumina, and is formed so as to cover upper and lower surfaces of the resistance heating element 72

One example of a method for manufacturing the NOx sensor 100 will be described below. First, six ceramic green sheets, not yet fired, are prepared. Then, patterns for the electrodes, the insulation layers, the resistance heating elements, etc. are printed and dried on the six ceramic green sheets corresponding respectively to the first substrate layer 1, the second substrate layer 2, the third substrate layer 3, the first solid electrolyte layer 4, the spacer layer 5, and the second solid electrolyte layer 6. Thereafter, those sheets are stacked to form a laminate. The laminate thus obtained includes a plurality of NOx sensors 100. The laminate is cut into pieces each corresponding to the size of one NOx sensor 100. A portion of an upper surface of each of the cut laminates, which portion operates as the outer pump electrode 23, is exposed to the outside. To cover the exposed portion, predetermined slurry is screen-printed thereon. The slurry is prepared by dispersing, in an organic solvent, a material that is used to form the characteristic stabilizing layer 24. Examples of the material include, as described above, an alumina porous body, a zirconia porous body, a spinel porous body, and a cordierite porous body. Such a porous body may be added with sodium, potassium, calcium, magnesium, barium, aluminum, zirconium, and/or silicon as required.

After the screen printing, the laminate is fired at a predetermined firing temperature, whereby the NOx sensor 100 is obtained.

With the NOx sensor 100 according to this embodiment described in detail above, since the outer pump electrode 23 is covered with the characteristic stabilizing layer 24 made of a porous body, the measurement accuracy can be maintained at a high level even when the ambient temperature of the sensor device 110 lowers abruptly. In addition, the light-off time can be prevented from becoming longer and from varying among products. More specifically, since the characteristic stabilizing layer 24 has a thickness of 10 μm or more and a sufficient thermal capacity, the temperature of the outer pump electrode 23 is not so reduced and the measurement accuracy is maintained at a high level even when the ambient temperature lowers abruptly. Also, since the thickness of the characteristic stabilizing layer 24 is 200 μm or less and the oxygen having been pumped out to the outer pump electrode 23 is evenly purged, the light-off time can be avoided from becoming longer. Further, if a variation in the thickness of the characteristic stabilizing layer 24 exceeds 20%, a variation in the light-off time among the products is increased abruptly. With such a thickness variation held to be 20% or less, however, the variation in the light-off time among the products can be held small.

Moreover, in the manufacturing process of the NOx sensor 100, the ceramic green sheets, not yet fired, are stacked to form the laminate. The predetermined slurry is screen-printed to cover a portion of the laminate, which operates as the outer pump electrode 23, and is then fired. Therefore, even when the layers 1 to 6 are warped during the firing, the outer pump electrode 23 and the characteristic stabilizing layer 24 are also warped correspondingly. In other words, the characteristic stabilizing layer 24 is deformed to follow the shapes of the second solid electrolyte layer 6 and the outer pump electrode 23. Hence, the characteristic stabilizing layer 24 the thickness of the characteristic stabilizing layer 24 is less apt to vary. As a result, it is easily possible to maintain not only the thickness of the characteristic stabilizing layer 24 in the range of 10 to 200 μm, but also to hold the variation in the thickness of the characteristic stabilizing layer 24 to be 20% or less.

It is needless to say that the present invention is in no way limited to the above-described embodiment, and that the present invention can be practiced in various embodiments without departing from the technical scope of the invention.

For example, while in the above-described embodiment the characteristic stabilizing layer 24 is formed to cover only the outer pump electrode 23, the characteristic stabilizing layer 24 may be formed to cover an entire upper surface of the NOx sensor 100, or to cover the entire upper surface and entire lateral surfaces (except the gas inlet port 10) of the NOx sensor 100, or to cover the entire upper surface, the entire lateral surfaces (except the gas inlet port 10), and an entire lower surface of the NOx sensor 100. As the NOx sensor 100 is covered with the characteristic stabilizing layer 24 in a larger area, the measurement accuracy can be more easily maintained at a high level even when the ambient temperature lowers abruptly.

Figure 2:
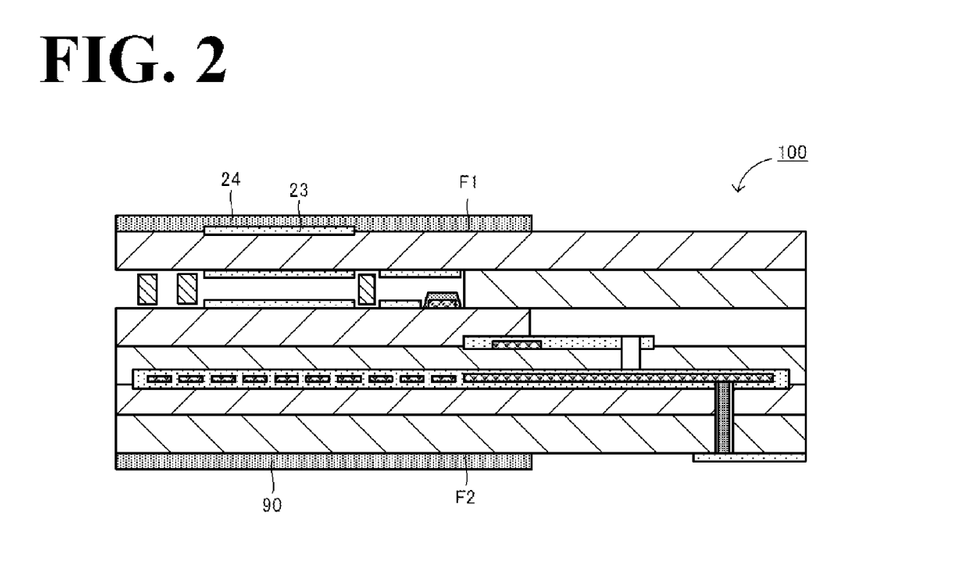
FIG. 2 is a sectional view illustrating principal components of a modification of the NOx sensor 100.
Figure 3:
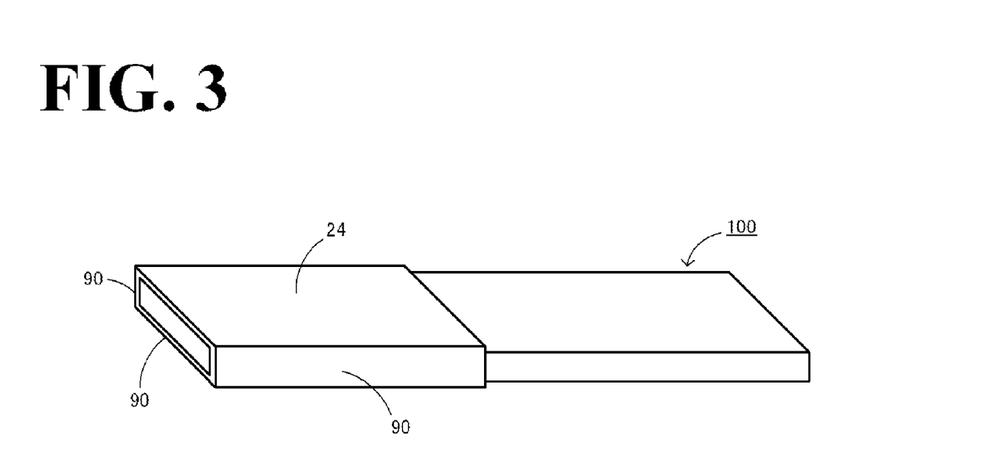
FIG. 3 is a perspective view of the modification of the NOx sensor 100.
Figure 4:
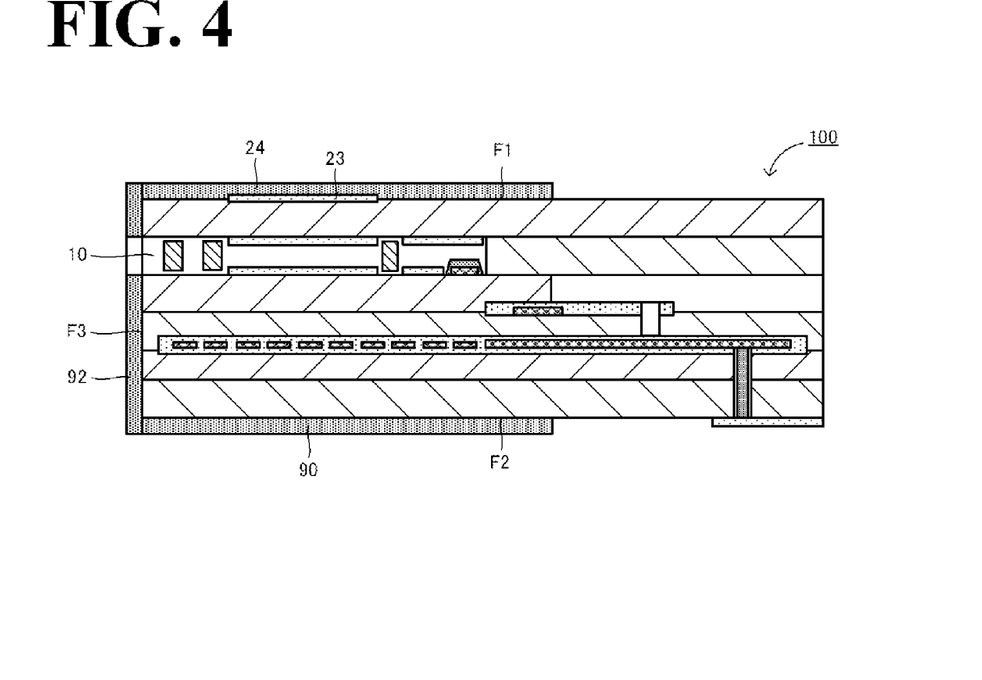
FIG. 4 is a sectional view illustrating principal components of another modification of the NOx sensor 100.
Figure 5:
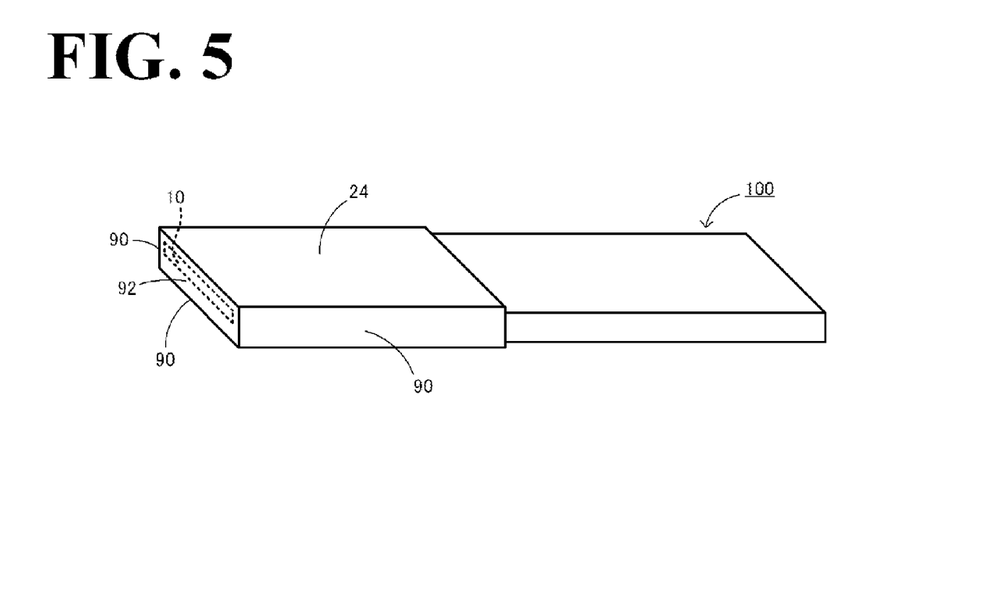
FIG. 5 is a perspective view of the other modification of the NOx sensor 100.

The foregoing embodiment has been described above in connection with the NOx sensor 100 including the characteristic stabilizing layer 24 to cover the outer pump electrode 23. As illustrated in FIG. 2, however, a firing strain prevention layer 90, which is similar to the characteristic stabilizing layer 24 in material, shape and thickness, may be formed, in addition to the characteristic stabilizing layer 24, on a surface F2 on the opposite side to a surface F1 on which the characteristic stabilizing layer 24 is formed. With such a modification, firing shrinkage occurs similarly in both the surface F1 on which the characteristic stabilizing layer 24 is formed and the surface F2 on the opposite side. Accordingly, even after a firing step in manufacturing the NOx sensor, the occurrence of a warp during the firing step can be prevented. The firing strain prevention layer 90 is preferably formed to be matched with a projected image resulting from projecting the characteristic stabilizing layer 24 onto the surface F2, i.e., to be positioned to oppositely face the characteristic stabilizing layer 24. The firing strain prevention layer 90 can be formed by, when the predetermined slurry is screen-printed in one example of the above-described method for manufacturing the NOx sensor 100, further screen-printing the predetermined slurry on the surface F2 on the opposite side to the surface F1 on which the outer pump electrode 23 is formed, in addition to the portion of the cut laminate, which operates as the outer pump electrode 23. Preferably, the firing strain prevention layer 90 is formed on not only the surface F2 on the opposite side to the surface F1 on which the characteristic stabilizing layer 24 is formed, but also all the lateral surfaces of the NOx sensor 100 (see FIG. 3). As a result, firing shrinkages occurred in four surfaces of the NOx sensor 100 become evener and resulting strains can be more surely prevented. Be it noted that the firing strain prevention layer 90 may differ from the characteristic stabilizing layer 24 in at least one of material, shape and thickness as long as the firing strain prevention layer 90 has the function of preventing firing distortions (warp and torsion) attributable to an imbalance in shrinkages during the firing, which imbalance is caused with the formation of the characteristic stabilizing layer 24. In addition to the firing strain prevention layer 90, as illustrated in FIG. 4, a thermal insulation layer 92 may be formed to cover a portion of a fore end surface F3 (i.e., a surface in which the gas inlet port 10 is provided) other than the gas inlet port 10. With such a modification, the thermal insulation effect is increased and the power consumption of the heater 70 can be further reduced. The thermal insulation layer 92 can be formed, for example, by using the same material as that of the characteristic stabilizing layer 24. FIG. 5 illustrates one example of the case where the firing strain prevention layer 90 is formed on the surface on the opposite side to the surface on which the characteristic stabilizing layer 24 is disposed and both the lateral surfaces of the NOx sensor 100, and the thermal insulation layer 92 is formed on the fore end surface thereof. The thermal insulation layer 92, illustrated in FIG. 5, is made of a porous body capable of introducing gas therethrough. Therefore, the thermal insulation layer 92 can be formed in a state covering the gas inlet port 10 without problems. The thermal insulation layer 92 can be formed by, before or after cutting the laminate of the ceramic green sheets into the shape corresponding to each of individual sensors, screen-printing the slurry and then firing the slurry (when the slurry is screen-printed before the cutting, the cutting step is performed before the firing).

While the NOx sensor 100 is manufactured in the above-described embodiment through the steps of printing and drying various patterns on the ceramic green sheets, stacking those ceramic green sheets to form a laminate, cutting the laminate into individual pieces, screen-printing the slurry to cover the portion of each of the cut laminates, which portion operates as the outer pump electrode 23, and firing the laminates after the screen printing, the NOx sensor 100 may be manufactured instead as follows. After printing and drying various patterns on the ceramic green sheets, the predetermined slurry is screen-printed on the ceramic green sheet having a portion, which operates as the outer pump electrode 23, to cover that portion. Then, the ceramic green sheets are stacked to form a laminate, which is cut into individual pieces each having the same size as that of one NOx sensor 100. The cut laminates are fired at a predetermined firing temperature, thereby obtaining the individual NOx sensors 100. In addition, the firing strain prevention layer 90 may be screen-printed to cover the portion of the NOx sensor 100 on the opposite side to the outer pump electrode 23 in a stage before stacking the ceramic green sheets.

EXAMPLES

Examples 1 to 12

The NOx sensors 100 of Examples 1 to 9 were manufactured according to the following basic procedures. First, six green sheets were fabricated by shaping a zirconia powder, added with 4 mol % of yttria as a stabilizer, into the form of a tape. Then, patterns for the electrodes, the insulation layers, the resistance heating elements, etc. were formed by screen printing on the six green sheets corresponding respectively to the first substrate layer 1, the second substrate layer 2, the third substrate layer 3, the first solid electrolyte layer 4, the spacer layer 5, and the second solid electrolyte layer 6 of the NOx sensor 100. Thereafter, those sheets were stacked and integrated to form a laminate. The laminate was cut into pieces each corresponding to the size of one NOx sensor 100. A portion of the upper surface of each of the cut laminates, the portion operating as the outer pump electrode 23, was exposed to the outside. The predetermined slurry was screen-printed to cover the exposed portion. The slurry used here was prepared by dispersing alumina powder, a binder, and an organic solvent with the aid of a pot mill. The slurry thus prepared had viscosity of 30 [Pa·s]. The laminate after the screen printing was fired at 1400° C. in atmospheric air, whereby the NOx sensor 100 was obtained. In the Examples 10 to 12, at the same time when the slurry was screen-printed on the portion, operating as the outer pump electrode 23, of the cut laminate, the slurry was further screen-printed on the surface of the NOx sensor on the opposite side to the portion operating as the outer pump electrode 23 and other lateral surfaces, as well as on the fore end surface (except the gas inlet port) thereof.

In the Example 1, the characteristic stabilizing layer 24 was not formed (namely, the thickness of the characteristic stabilizing layer 24 was 0 μm). In the Examples 2 to 9, the screen printing of the slurry was performed to form the characteristic stabilizing layers 24 in thicknesses of 5 μm, 10 μm, 20 μm, 50 μm, 100 μm, 120 μm, 200 μm, and 300 μm, respectively. In the Examples 10 to 12, the thickness of each characteristic stabilizing layer 24 was set to be the same as that of the firing strain prevention layer and the thermal insulation layer, and the screen printing of the slurry was performed to form the characteristic stabilizing layers 24 in thicknesses of 10 μm, 100 μm and 200 μm. The characteristic stabilizing layer 24 was formed by adjusting the thickness of a mask for use in the screen printing when the thickness was in the range of 5 to 20 μm, and by adjusting the number of repetitions of the screen printing when the thickness was 50 μm or more. The characteristic stabilizing layer 24 thus formed had a thickness variation of about and a porosity of 25 to 35%. Be it noted that the Examples 3 to 8 and 10 to 12 correspond to the embodiment of the present invention and the Examples 1, 2 and 9 correspond to comparative examples.

NOx Sensitivity Ratio

Figure 6:
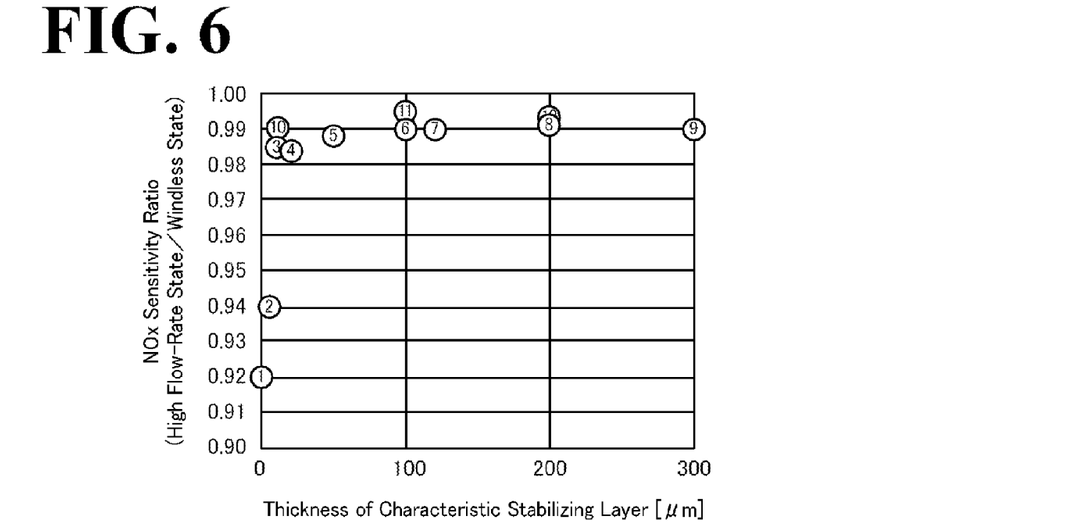
FIG. 6 is a graph illustrating the relationship between a thickness of a characteristic stabilizing layer and a NCH sensitivity ratio.

A NOx sensitivity ratio was determined by using each of the NOx sensors 100 of the Examples 1 to 12. More specifically, the NOx sensitivity ratio was determined as X1/X0 on condition that a measured value resulting from measuring the gas to be measured, in which the concentration of NOx had been previously adjusted to a predetermined value, in a windless state (0.1 msec or less) was NO and a measured value resulting from measuring the same gas to be measured after 3 minutes from the time of starting the gas to be measured to flow at a flow rate of 15 m/sec was X1. The measured results are plotted in FIG. 6. As seen from a graph of FIG. 6, when the thickness of the characteristic stabilizing layer 24 is 10 μm or more, sensitivity comparable to that in the windless state is obtained even in the high flow-rate state. The reason presumably resides in that, when the thickness of the characteristic stabilizing layer 24 is 10 μm or more, the thermal capacity of the characteristic stabilizing layer 24 is sufficiently large and hence the temperature of the outer pump electrode 23 is not so reduced even if the ambient temperature lowers abruptly due to a wind of the gas flowing at the high flow rate. In the Examples 10 to 12, the NOx sensitivity ratio is increased in comparison with that in the Examples 3, 6 and 8. The reason presumably resides in that the thermal insulation effect is further increased with the provision of one or both of the firing strain prevention layer and the thermal insulation layer.

Device Temperature Stability Index

Figure 7:
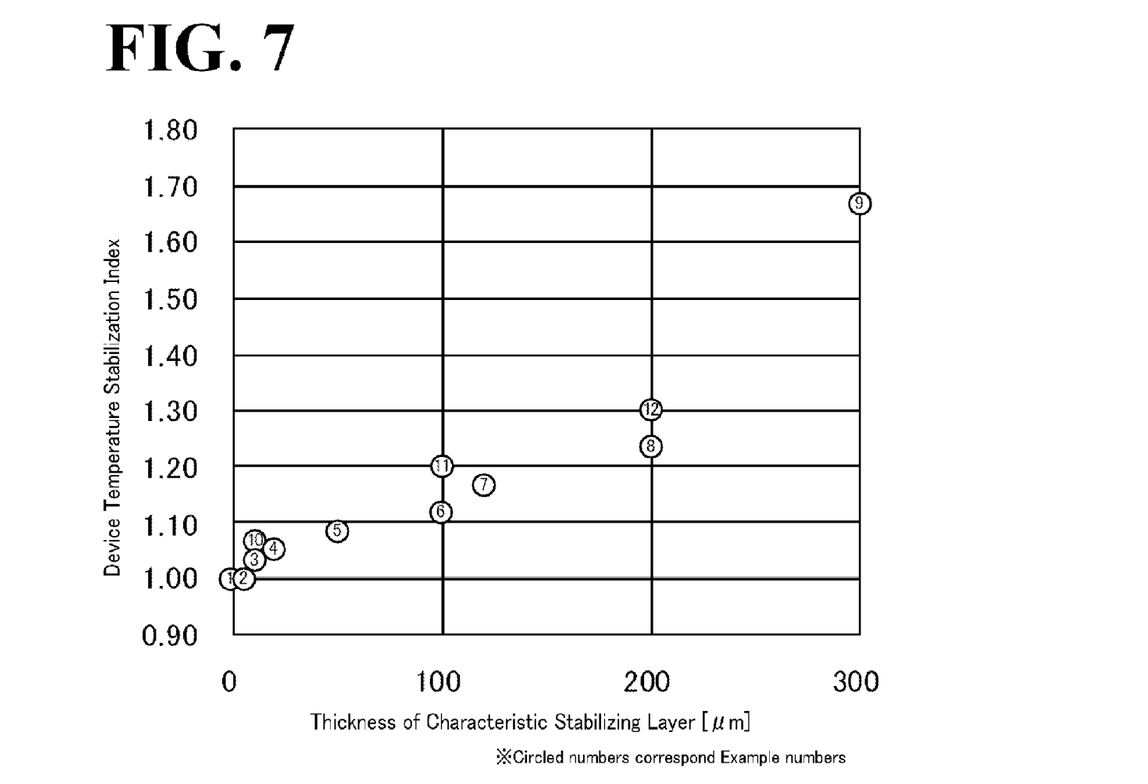
FIG. 7 is a graph illustrating the relationship between the thickness of the characteristic stabilizing layer and a device temperature stabilization index.

Device temperature stability indexes were determined by using the NOx sensors 100 of the Examples 1 to 12. More specifically, a signal stabilizing time taken for impedance between the outer pump electrode 23 and the inner pimp electrode 22 to stabilize was measured on condition that the temperature of each NOx sensor 100 was raised in accordance with a certain heater temperature rise pattern (herein, a pattern for raising the temperature to reach a setting value in about 40 sec), and a ratio of the measured time for each of the Examples 2 to 12 to the measured time for the Example 1 was obtained as the device temperature stability index. The measured results are plotted in FIG. 7. As seen from a graph of FIG. 7, when the thickness of the characteristic stabilizing layer 24 is 200 μm or less, the device temperature stability index is 1.25 or less (particularly, when it is 100 μm or less, the device temperature stability index is 1.2 or less). However, when the thickness of the characteristic stabilizing layer 24 exceeds 200 μm, the device temperature stability index is abruptly increased. The reason presumably resides in that when the thickness of the characteristic stabilizing layer 24 is 200 μm or less, the purging of the oxygen having been pumped out to the outer pump electrode 23 is even and a long time is not required for the impedance to stabilize, but when the thickness of the characteristic stabilizing layer 24 exceeds 200 the purging of the oxygen having been pumped out to the outer pump electrode 23 becomes uneven and a long time is required for the impedance to stabilize. Be it noted that the time required for the impedance to stabilize can be regarded as being the same as the light-off time.

Examples 13 to 17

In the Examples 13 to 17, before firing the laminate, the characteristic stabilizing layers 24 were each formed by the screen printing method in accordance with the above-described basic procedures such that the thickness of the characteristic stabilizing layer 24 has an average value of 50 μm. On that occasion, the number of repeated printings, the viscosity of the slurry, etc. were adjusted as appropriate to form the characteristic stabilizing layers 24 with thickness variations of 5%, 10% and 20%. On the laminate after the firing, it was likewise tried to form the characteristic stabilizing layers with thickness variations of 5%, 10% and 20%. However, the thickness variation of less than 30% was not obtained. In other words, only the characteristic stabilizing layers with thickness variations of 30% or more were obtained even when the number of repeated printings, the viscosity of the slurry, etc. were adjusted. The reason presumably resides in that the printed surface is not even due to warp, a recess, etc. after the firing of the laminate, while the slurry used in the screen printing method has fluidity so as to form an even upper surface, thus causing a large thickness variation. The NOx sensor including the characteristic stabilizing layer with the thickness variation of 30% was defined as the Example 16. Further, in order to form the characteristic stabilizing layers with thickness variations of to 50%, it was tried to dip the laminates after the firing in the slurry (while a tape was applied to the surface of the laminate other than a region where the characteristic stabilizing layer was to be formed, to thereby prevent the slurry from being attached to that region). However, the characteristic stabilizing layer with the thickness variation of less than 50% was not obtained in spite of variously adjusting the viscosity of the slurry and changing a drying method after the dipping. The reason presumably resides in that, due to fluidity of the slurry, the upper surface of the characteristic stabilizing layer is apt to fluctuate depending on the direction of the laminate left to stand and a handling method for the laminate after the dipping. The NOx sensor including the characteristic stabilizing layer with the thickness variation of was defined as the Example 17. The thickness variation was determined through the steps of measuring, when cross-sections of the sensor device in the lengthwise direction thereof were observed with an SEM in opposite end portions and a central portion of the outer pump electrode, thicknesses between the surface of the characteristic stabilizing layer in the opposite end portions and the central portion of the outer pump electrode and the interface between the outer pump electrode and the characteristic stabilizing layer at five points in each of the cross-sections, calculating a difference R between a maximum value and a minimum value and an average value Av of the measured thicknesses, and obtaining a value in terms of percentage by dividing the difference R by the average value Av (see the following formula).

$$\text{Thickness variation (\%)} = R/Av \times 100$$

Herein, the thickness is defined through the steps of by setting, as a field of view, an area with a width of 100 μL at each measurement point, extracting a curved line representing the surface of the characteristic stabilizing layer and a curved line representing the interface between the outer pump electrode and the characteristic stabilizing layer in the field of view through image analysis, and determining the distance of an arbitrary perpendicular line extending from an approximate linear line, which is obtained from the curved line representing the surface of the characteristic stabilizing layer based on the least square method, to the curved line representing the interface between the outer pump electrode and the characteristic stabilizing layer.

Variation in Signal Stabilizing Time

Five NOx sensors 100 were manufactured for each of the Examples, and the temperature of each NOx sensor was raised in atmospheric air according to the certain heater temperature rise pattern (herein, the pattern for raising the temperature to reach the setting value in about 40 sec). Thereafter, a time taken for an output signal to stabilize after the start of driving of each pump electrode was measured. Then, a variation in the signal stabilizing time per Example was determined based on the following formula. In the following formula, Tmax, Tmin and Tavr denote a maximum value, a minimum value and an average value, respectively, among the signal stabilizing times measured for the five NOx sensors 100 of the same Example. The measured results of the Examples 13 to 17 are plotted in FIG. 8. Be it noted that the Examples 13 to 15 correspond to the embodiment of the present invention and the Examples 16 and 17 correspond to comparative examples.

Variation (%) in signal stabilizing time=(*T*max−*T*min)/*T*avr×100

Figure 8:
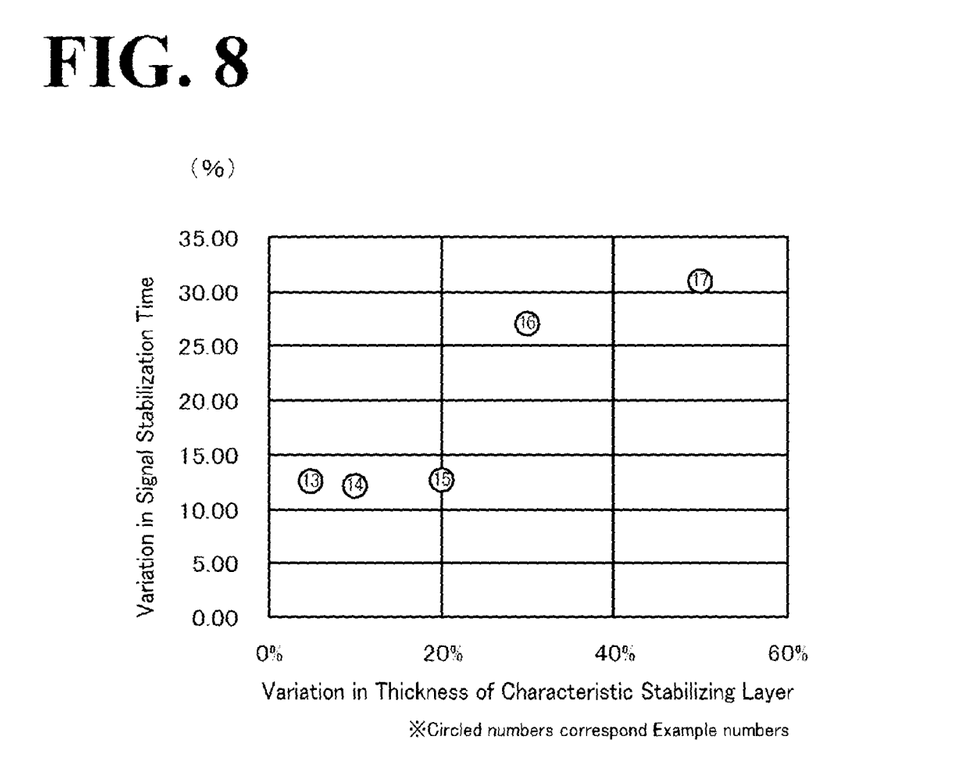
FIG. 8 is a graph illustrating the relationship between a variation in the thickness of the characteristic stabilizing layer and a variation in a signal stabilization time.

As seen from a graph of FIG. 8, when the thickness variation of the characteristic stabilizing layer 24 is 20% or less, the variation in the signal stabilizing time is as low as in the range of 10 to 15%. On the other hand, when the thickness variation of the characteristic stabilizing layer 24 exceeds 20%, the variation in the signal stabilizing time is abruptly increased. Since the signal stabilizing time can be regarded as being the same as the light-off time, it is understood that when the thickness variation of the characteristic stabilizing layer 24 is 20% or less, a variation in the light-off time among the products can be held low.

With regard to the manufacturing method for the NOx sensor 100, when the characteristic stabilizing layer 24 is formed by the dipping, it is more difficult to hold even the thickness of the slurry than the case of using the screen printing, and hence the thickness variation of the characteristic stabilizing layer 24 is excessively increased. Also, when the characteristic stabilizing layer 24 is formed by the screen printing on the laminate after the firing, a warp occurs in the laminate during the firing and a printed pattern cannot follow the surface of the laminate, whereby the thickness variation of the characteristic stabilizing layer 24 is excessively increased. In contrast, when the characteristic stabilizing layer 24 is formed by the screen printing on the laminate before the firing, the thickness variation of the characteristic stabilizing layer 24 is less apt to occur for the reason that even if the laminate is warped during the firing, the outer pump electrode 23 and the characteristic stabilizing layer 24 are also warped correspondingly. For the same reason, when the firing strain prevention layer 90 and the thermal insulation layer 92 are formed, the screen printing is preferably performed on the laminate before the firing.

While the present invention has been described primarily in connection with the NOx sensor, the scope of the present invention is not limited to such an application. More specifically, the present invention is applicable to a gas sensor which includes an electrochemical cell constituted by using a solid electrolyte, and which requires, from a structural point of view, an electrode (i.e., the outer pump electrode) disposed in a region differing the region where an electrode for detecting a gas (i.e., the inner pump electrode) is disposed. An $O_2$ sensor, for example, differs from the NOx sensor only in a point that $O_2$ is decomposed at the inner pump electrode instead of NOx, and it operates based on the same detection principle as that described above, namely on the principle that oxygen is pumped out from the inner pump electrode through the outer pump electrode. Further, an $NH_3$ sensor of the type oxidizing $NH_3$ to generate NOx and pumping out oxygen generated upon decomposition of the NOx to detect the oxygen utilizes the same principle as that in the NOx sensor. Therefore, coating the characteristic stabilizing layer on the outer pump electrode to detect each of those gases have the same object, construction and advantages as those in the NOx sensor referred to above for explaining the present invention. In addition, similar advantages are also obtained when handling other gas species of the type containing oxygen atom(s), such as $CO_2$ and $H_2O$.

The present application claims priority from the Japanese Patent Application No. 2010-021430 filed on Feb. 2, 2010, the entire contents of which are incorporated herein by reference.

What is claimed is:

1. A gas sensor comprising a sensor device including a gas inlet port, an inner pump electrode in communication with the gas inlet port, and an outer pump electrode disposed respectively on an inner side and an outer side of a base member made of a solid electrolyte layer having oxygen-ion conductivity, the sensor device detecting concentration of a particular gas in an object gas to be measured with operations of introducing the object gas through a gas inlet port into a gas chamber to which the inner pump electrode is exposed and pumping out oxygen in the gas chamber to the outside from the inner pump electrode through the outer pump electrode, and a heater disposed adjacent to the sensor device to be capable of heating the sensor device,
wherein the gas inlet port includes an opening on an outermost external surface of the base member,
wherein the gas sensor further comprises (i) a characteristic stabilizing layer that is spaced from the opening of the gas inlet port on a plane perpendicular to the outermost external surface of the base member, so as to cover the outer pump electrode, said characteristic stabilizing layer being made of a porous body with a thickness of 10 to 200 μm and a thickness variation of 20% or less, and (ii) a thermal insulation layer formed only on the outermost external surface plane of the base member so as to cover the opening of the gas inlet port, and wherein the thermal insulation layer covers the entirety of the outermost external surface of the base member.

2. The gas sensor according to claim 1, wherein the particular gas is NOx.

3. The gas sensor according to claim 1, wherein the characteristic stabilizing layer has a thickness of 10 to 100 μm.

4. The gas sensor according to claim 1, further comprising a firing strain prevention layer formed on a surface of the sensor device opposite to a surface thereof on which the characteristic stabilizing layer is provided.

5. A method for manufacturing the gas sensor according to claim 4, the method comprising the steps of:
(a) preparing a plurality of unfired green sheets used to form the sensor device and the heater;
(b) stacking the unfired green sheets to form a laminate, and screen-printing slurry as a material forming the characteristic stabilizing layer, to cover a portion of the laminate with the slurry, the portion serving as the outer pump electrode; and
(c) firing the laminate obtained in the step (b),
wherein the step (b) further performs screen-printing slurry as a material forming the firing strain prevention layer to cover a portion of the laminate with the slurry, the portion serving as the firing strain prevention layer, after stacking the unfired green sheets to form a laminate.

6. A method for manufacturing the gas sensor according to claim 4, the method comprising the steps of:
(a) preparing a plurality of unfired green sheets used to form the sensor device and the heater;
(b) screen-printing slurry as a material forming the characteristic stabilizing layer on one of the unfired green sheets, which includes a portion serving as the outer pump electrode, to cover the portion with the slurry, and thereafter stacking the unfired green sheets to form a laminate; and (c) firing the laminate obtained in the step (b),
wherein the step (b) further performs screen-printing slurry as a material forming the firing strain prevention layer on at least one surface of one or more of the unfired green sheets, on which the firing strain prevention layer is to be formed, prior to stacking the unfired green sheets to form a laminate.

7. The gas sensor according to claim 4, wherein the firing strain prevention layer is further formed on both lateral surfaces sandwiched between the surface of the sensor device on which the characteristic stabilizing layer is disposed and the surface thereof opposite to the former surface.

8. A method for manufacturing the gas sensor according to claim 7, the method comprising the steps of:
   (a) preparing a plurality of unfired green sheets used to form the sensor device and the heater;
   (b) stacking the unfired green sheets to form a laminate, and screen-printing slurry as a material forming the characteristic stabilizing layer, to cover a portion of the laminate with the slurry, the portion serving as the outer pump electrode; and
   (c) firing the laminate obtained in the step (b),
   wherein the step (b) further performs screen-printing slurry as a material forming the firing strain prevention layer to cover a portion of the laminate with the slurry, the portion serving as the firing strain prevention layer, after stacking the unfired green sheets to form a laminate.

9. A method for manufacturing the gas sensor according to claim 7, the method comprising the steps of:
   (a) preparing a plurality of unfired green sheets used to form the sensor device and the heater;
   (b) screen-printing slurry as a material forming the characteristic stabilizing layer on one of the unfired green sheets, which includes a portion serving as the outer pump electrode, to cover the portion with the slurry, and thereafter stacking the unfired green sheets to form a laminate; and
   (c) firing the laminate obtained in the step (b),
   wherein the step (b) further performs screen-printing slurry as a material forming the firing strain prevention layer on at least one surface of one or more of the unfired green sheets, on which the firing strain prevention layer is to be formed, prior to stacking the unfired green sheets to form a laminate.

10. A method for manufacturing the gas sensor according to claim 1, the method comprising the steps of:
   (a) preparing a plurality of unfired green sheets used to form the sensor device and the heater;
   (b) stacking the unfired green sheets to form a laminate, and screen-printing slurry as a material forming the characteristic stabilizing layer, to cover a portion of the laminate with the slurry, the portion serving as the outer pump electrode; and
   (c) firing the laminate obtained in the step (b).

11. A method for manufacturing the gas sensor according to claim 1, the method comprising the steps of:
   (a) preparing a plurality of unfired green sheets used to form the sensor device and the heater;
   (b) screen-printing slurry as a material forming the characteristic stabilizing layer on one of the unfired green sheets, which includes a portion serving as the outer pump electrode, to cover the portion with the slurry, and thereafter stacking the unfired green sheets to form a laminate; and
   (c) firing the laminate obtained in the step (h).

* * * * *